(12) United States Patent
Huene

(10) Patent No.: US 8,486,084 B2
(45) Date of Patent: Jul. 16, 2013

(54) SURGICAL SLAP HAMMER

(76) Inventor: Donald Huene, Fresno, CA (US)

( * ) Notice: Subject to any disclaimer, the term of this patent is extended or adjusted under 35 U.S.C. 154(b) by 366 days.

(21) Appl. No.: 12/821,582

(22) Filed: Jun. 23, 2010

(65) Prior Publication Data

US 2010/0331851 A1 Dec. 30, 2010

Related U.S. Application Data

(60) Provisional application No. 61/219,866, filed on Jun. 24, 2009.

(51) Int. Cl.
| | |
|---|---|
| A61B 17/58 | (2006.01) |
| A61B 17/60 | (2006.01) |
| A61F 2/00 | (2006.01) |
| B25D 1/00 | (2006.01) |
| B25D 1/16 | (2006.01) |
| B25D 9/00 | (2006.01) |
| B25D 11/00 | (2006.01) |
| B25D 13/00 | (2006.01) |
| B25D 16/00 | (2006.01) |
| B25C 7/00 | (2006.01) |
| B25C 11/00 | (2006.01) |
| B23B 45/16 | (2006.01) |
| E21B 1/00 | (2006.01) |
| B66F 15/00 | (2006.01) |

(52) U.S. Cl.
USPC ............ 606/100; 81/27; 227/146; 173/128; 173/129; 173/133; 173/202; 254/19

(58) Field of Classification Search
USPC ............ 606/100; 81/27; 227/146; 173/128, 173/129, 133, 202; 254/19
See application file for complete search history.

(56) References Cited

U.S. PATENT DOCUMENTS

| | | | | |
|---|---|---|---|---|
| 1,747,053 | A | * | 2/1930 | Colerick ...................... 254/19 |
| 2,337,971 | A | * | 12/1943 | Caviglia ..................... 433/151 |
| 2,421,354 | A | | 5/1947 | Reiter |
| 2,437,014 | A | | 3/1948 | Arnesen et al. |
| 2,725,878 | A | | 12/1955 | Reiter |
| 3,030,837 | A | * | 4/1962 | Chartier ....................... 72/457 |
| 3,169,010 | A | * | 2/1965 | Crawford, Jr ................. 254/19 |
| 3,791,012 | A | * | 2/1974 | Jenkin ......................... 29/254 |
| 4,307,635 | A | * | 12/1981 | Genova ........................ 81/463 |
| 4,669,341 | A | * | 6/1987 | Small .......................... 81/418 |
| 5,282,805 | A | | 2/1994 | Richelsoph et al. |
| 5,398,861 | A | * | 3/1995 | Green ...................... 227/175.1 |
| 5,571,111 | A | | 11/1996 | Aboczky |
| 5,735,855 | A | | 4/1998 | Bradley |
| 5,827,290 | A | | 10/1998 | Bradley |
| 5,984,272 | A | * | 11/1999 | Crider ......................... 254/18 |
| 6,010,508 | A | | 1/2000 | Bradley |

(Continued)

*Primary Examiner* — Kevin T Truong
*Assistant Examiner* — David Bates
(74) *Attorney, Agent, or Firm* — Berenato & White, LLC

(57) ABSTRACT

A slap hammer including an adjustable striking member and a releasable retaining mechanism for releasably retaining a sliding weight is disclosed. One described slap hammer comprises a guide rod having a first end and a second end; a striking member coupled to the second end of the guide rod and movable relative to the first end of the guide rod; a sliding weight slidable along the guide rod between the first end of the guide rod and the striking member; a biasing element positioned between the sliding weight and the first end of the guide rod, the biasing element biasing the sliding weight towards the second end of the guide rod; and a releasable retaining mechanism for releasably retaining the sliding weight against the action of the biasing element.

9 Claims, 4 Drawing Sheets

U.S. PATENT DOCUMENTS

| | | |
|---|---|---|
| 6,349,618 B1 | 2/2002 | Lowther |
| 6,709,439 B2 | 3/2004 | Rogers et al. |
| 7,036,211 B1 * | 5/2006 | Panks .............................. 29/718 |
| 2006/0178673 A1 * | 8/2006 | Curran .......................... 606/100 |

* cited by examiner

SURGICAL SLAP HAMMER

CROSS-REFERENCE TO RELATED APPLICATIONS AND CLAIM TO PRIORITY

This patent application claims the benefit of U.S. Provisional Application No. 61/219,866, entitled "Slap Hammer," and filed Jun. 24, 2009, the entirety of which is incorporated herein and to which priority is claimed.

FIELD OF THE INVENTION

The present disclosure relates to a surgical instrument, known as a slap hammer, and more particularly to a slap hammer including a biasing element, a releasable retaining mechanism for releasably retaining the sliding weight against the biasing element, and an adjustable striking member. The slap hammer is used by a surgeon to remove articles embedded in bone, such as a prosthetic.

BACKGROUND OF THE INVENTION

Injuries, disease, as well as the natural aging process, can lead to changes in the musculoskeletal system of the body—i.e. the bones, joints, and muscles of the body. Such changes, or injuries, can manifest in physical degeneration. To correct such damage, medical practitioners routinely perform various orthopedic procedures.

Routine orthopedic procedures include hip replacement and knee replacement surgery. During replacement of a joint such as the hip or knee, diseased or damaged joint surfaces are replaced with metal and plastic components shaped to allow continued use (and motion) of the joint. After incisions are made for surgical access, damaged or diseased materials, such as bones and muscles, are removed, with artificial prostheses inserted in their place. Additionally, it is often necessary to remove surgical implements that are secured to a patient. However, access to the surgical implements may be limited due to the confines of the surgical operating workspace.

Several different tools are used during orthopedic procedures to place and/or remove various objects. Mallets are frequently used to apply an impacting force on a medical tool, such as a chisel, to remove bones or other implanted objects. Mallets are also commonly used to insert an implant, and to remove tools positioned in the surgical area. While mallets are effective, the impacting force must be axially applied to avoid misalignment of the prosthesis, or the inadvertent removal of bone. Moreover, the force applied must be sufficiently controlled for avoiding damage to the bone.

To overcome some of these problems, slap hammers have been developed and are widely used in orthopedic procedures to apply an impacting force on various tools used during surgery. Slap hammers typically consist of a guide rod and a sliding weight. One end of the guide rod is affixed to an object or surface, such as a surgical implement. The sliding weight may be thrown upward, generating a jerking force when the sliding weight strikes a stop on the end of the guide rod. The sliding weight may be repeatedly "thrown" to extract the surgical implement. Alternatively, when the slap hammer is affixed to a loose object or surface, the hammer may be dropped or thrown downward toward the object for a precision impact.

Conventional slap hammers, however, may not deliver a controlled, consistent, and optimal impact force. Thus, there is a need for a more effective and convenient slap hammer tool.

BRIEF SUMMARY OF THE INVENTION

In accordance with one embodiment, a slap hammer comprises a guide rod having a first end and a second end, a striking member coupled to the second end of the guide rod and movable relative to the first end of the guide, a sliding weight slidable along the guide rod between the first end of the guide rod and the striking member, and a biasing element positioned between the sliding weight and the first end of the guide rod and biasing the sliding weight towards the second end of the guide rod. The embodiment further comprises a releasable retaining mechanism for releasably retaining the sliding weight against the action of the biasing element.

In accordance with another embodiment, a method for using a slap hammer to apply a force to an object comprises coupling a guide rod to an object, sliding a sliding weight along the guide in the direction of the object and against the bias of a biasing element, mechanically retaining the sliding weight against the biasing element, and mechanically releasing the sliding weight to cause the sliding weight to slide along the guide in a direction away from the object and to deliver an impact to the striking member.

The presently disclosed slap hammer provides numerous advantages in the art. For example, the disclosed slap hammer allows a user to have greater control over the force of the hammer strike than in conventional slap hammers. Specifically, disclosed slap hammers can deliver variable forces, allowing a single device to deliver a range of controlled impact forces.

Other aspects of the invention, including apparatus, systems, methods, and the like which constitute part of the invention, will become more apparent upon reading the following detailed description of the exemplary embodiments and viewing the drawings.

BRIEF DESCRIPTION OF THE DRAWINGS

The accompanying drawings are incorporated in and constitute part of the specification. The drawings, together with the general description given above and the detailed description of the exemplary embodiments and methods given below, serve to explain the principles of the invention. In such drawings.

DETAILED DESCRIPTION OF THE PREFERRED EMBODIMENTS

Figure 1:
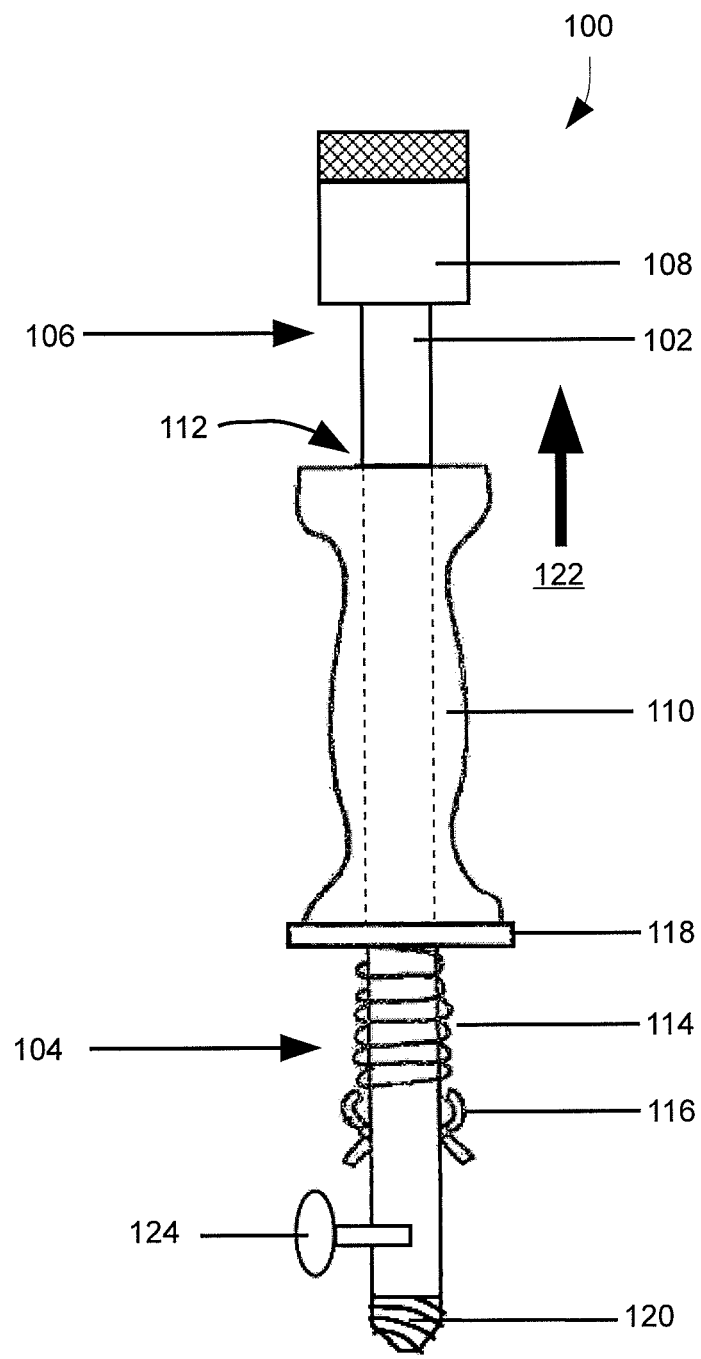
FIG. 1 is a plan view an illustration of a slap hammer according to an embodiment of the invention.

Reference will now be made in detail to exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the exemplary embodiments and methods. The invention according to its various aspects is particularly pointed out and distinctly claimed in the attached claims read in view of this specification, and appropriate equivalents.

FIG. 1 is an illustration of a slap hammer device 100 according to an embodiment of the invention. The slap hammer 100 includes a uniform diameter guide rod 102 having a first end 104 and a second end 106. The slap hammer 100 also includes a sliding weight 110 that is slidable along the guide rod 102. Sliding weight 110 has a uniform diameter opening 112 extending its length in order to allow the sliding action along the guide rod 102. The slap hammer 100 is used to apply a force to an object (not shown) coupled to the first end 104 of the guide rod 102.

The guide rod 102 can be coupled to an object, such as a surgical implement, prosthesis, or body part, in a variety of ways. As shown in FIG. 1, the first end 104 of the guide rod 102 comprises a screw coupling mechanism 120. The screw coupling mechanism 120 comprises a threaded end configured to mate with a threaded portion of a surgical implement. Other coupling mechanisms include pliers, a hook, a clamp, a ring, a magnet, and like coupling mechanisms. Still other coupling mechanisms may be used, such as a snap fit or friction fit connection. In some scenarios, a removable or interchangeable coupling mechanism may be desirable, so that the slap hammer may be quickly disconnected from one surgical implement and connected to another. In other embodiments a more permanent coupling is used to provide greater stability and rigidity.

A striking member 108 is coupled to the second end 106 of the guide rod 102. During operation of the slap hammer 100, the sliding weight 110 impacts the striking member 108 as it travels from the first end 104 of the guide rod 102 toward the second end 106 of the guide rod 102 in the direction of arrow 122. The position of the striking member 108 may be adjusted relative to the first end 104 of the guide rod 102. For example, the striking member 108 may be moved towards or away from the first end 104 of the guide rod 102.

The force delivered by the slap hammer 100 on an object can be advantageously controlled by adjusting or moving the striking member 108. Moving the striking member 108 closer to the first end 104 of the guide rod 102 may limit the speed and acceleration of the striking member 108 as it is pushed by the biasing element 114. Alternatively, moving the striking member 108 away from the first end 104 of the guide rod 102 may allow the striking member 108 to accelerate more as it is pushed by the biasing element 114, thereby imparting a greater striking force when the sliding weight strikes the striking member 108.

The striking member 108 may have a variety of configurations. The striking member 108 can be threadedly coupled to the second end 106 of the guide rod 102. In such an embodiment, the position of the striking member 108 on the guide rod 102 may be adjusted merely by spinning or rotating the striking member 108 about the guide rod 102. Alternatively, the striking member 108 can be coupled to the second end 106 of the guide rod 102 in other ways, such as with a latching mechanism. The latching mechanism may catch or latch onto specific predetermined stops located along the second end 106 of the guide rod 102. In this manner, the striking force of the slap hammer 100 may be discretely predefined at each individual stop. In the embodiment illustrated in FIG. 1, the striking member has a circular cross-section. However, the striking member may also have other geometric or irregular cross-sections.

As shown in FIG. 1, the sliding weight 110 moves, or slides, along the guide rod 102 via an opening 112 in the sliding weight 110. The guide rod 102 extends through the opening 112, and the sliding weight can move toward and away from the first end 104 of the guide rod 102. In other embodiments, a sliding weight may attach to the side of a guide rod, and move alongside the guide rod, or move inside a cylindrical chamber or conduit which contains all or part of the slap hammer 100.

A biasing element, illustrated in FIG. 1 as a spring biasing element 114, is positioned about the guide rod 102 at the first end 104 of the guide rod 102. The spring biasing element 114 comprises a cylindrical compression spring designed to resist applied compression force and to store energy in a compressed stance. The biasing element may comprise other biasing mechanisms, such as a tensioning spring. As the sliding weight 110 is moved toward the first end 104 of the guide rod 102, the spring biasing element 114 is compressed to store energy and biases the sliding weight 110 in the opposite direction, towards the second end 106 of the guide rod 102.

A releasable retaining mechanism 116 releasably retains the sliding weight 110 against the bias, or action of the spring biasing element 114. A triggering mechanism 124 for mechanically triggering the release of the sliding weight 110 is coupled to the releasable retaining mechanism 116. The triggering mechanism 124, shown as a trigger button, may be pressed or activated by an operator to mechanically activate the releasable retaining mechanism 116, releasing the sliding weight 110 which is propelled by the spring biasing element 114 in the direction of arrow 122 towards the striking member 108.

The sliding weight 110 is adapted to move along the guide rod 102 between the releasable retaining mechanism 116 at the first end 104 and the striking member 108 at the second end 106. The spring biasing element 114 is disposed between the sliding weight 110 and the releasable retaining mechanism 116 and urges the sliding weight 110 in the direction of the striking member 108. The sliding weight 110 may be urged against the action of the spring 114 and locked in place via the releasable retaining mechanism 116.

The retaining mechanism 116 may have any number of configurations for releaseably retaining the sliding weight 110 against the biasing element 114. As shown in FIG. 1, the releasable retaining mechanism 116 comprises a pair of pivoting hooks which restrain the sliding weight 110 against the action of the spring biasing element 114. The pivoting hooks are pivotably coupled to the first end 104 of the guide rod 102. The pivoting hooks releaseably engage the sliding weight 110 to retain the sliding weight 110 against the action of the spring 114. The sliding weight 110 also includes an engaging mechanism 118, shown in FIG. 1 as a collar. The engaging mechanism 118 of the sliding weight 110 engages the retaining mechanism 116 of the guide rod 102 to hold the sliding weight 110 in place, against the bias of the spring biasing element 114. To operate the slap hammer, the hooks are pivoted out of engagement with the collar, thereby releasing the sliding weight 110 and allowing the spring biasing element 114 to urge the sliding weight 110 in the direction of the striking member 108.

Other types of releasable retaining mechanisms may be used to releaseably retain the sliding weight 110 against the spring biasing element 114, such as a latch mechanism as used in umbrellas. In some devices, the sliding weight 110 is restrained in direct contact with the spring 114. In other devices, the sliding weight 110 is restrained in indirect contact with the spring 114, but still against the action, or bias, of the spring 114.

Devices according to embodiments of the present invention may be fabricated from light, strong and rigid biocompatible materials. For example, in some embodiments, the slap hammer may comprise metal, metal alloys, polymeric composites or other known suitable materials. In some embodiments, various components or the entire slap hammer may be disassembled or taken apart for storage and/or cleaning. In some embodiments, biasing elements of differing strengths, or tensions, may be utilized, to provide varying forces on objects coupled to the slap hammer.

Various slap hammers may be configured in many different dimensions, and deliver a wide range of impact forces. In some embodiments, the slap hammer may be dimensioned for delivering substantially large impact forces and in other embodiments, the slap hammer may be dimensioned for delivering lesser impact forces. Advantageously, the adjustable striking member 108 allows slap hammers 100 of any dimension to deliver a wide range of impact forces.

Figure 2A:
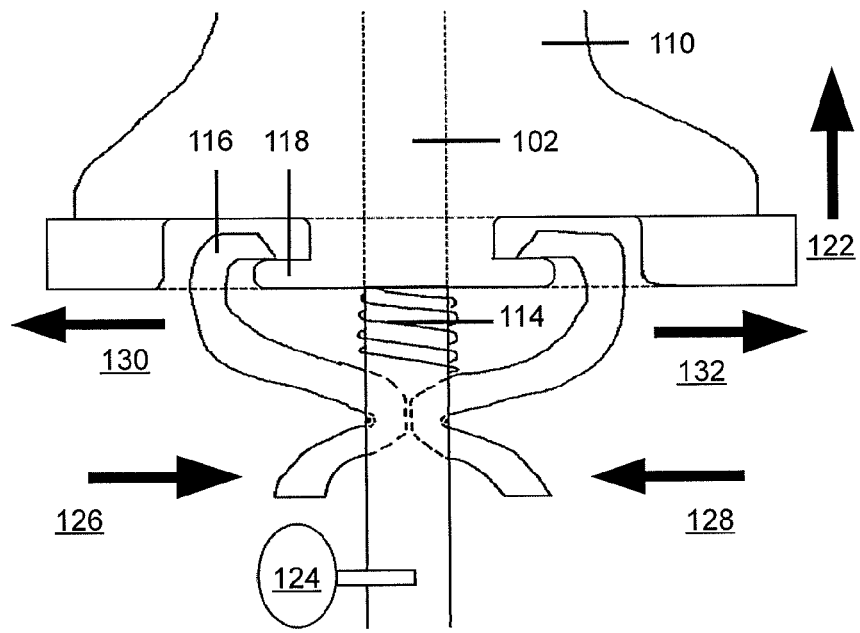
FIG. 2a is a fragmentary cross sectional illustration of a slap hammer according to the embodiment illustrated in FIG. 1.

FIG. 2a is a fragmentary cross sectional view of a slap hammer according to the embodiment. The releasable retaining mechanism 116 engages the engaging mechanism 118 of the sliding weight 110, thereby holding the sliding weight 110 in place against the action of the spring biasing element 114. The releasable retaining mechanism 116 comprises a pair of pivoting hooks. The base or legs of the pivoting hooks can be pinched inward, or acted on the direction of arrows 126, 128. As each leg of each pivoting hook is pinched inward, each arm of each pivoting hook pivots about a pivot axis, and moves outward in the direction of arrows 130, 132. As the arms of the pivoting hooks pivot outward, the engaging mechanism 118 is released from the retaining mechanism 116, sending the sliding weight 110 toward the second end of the guide rod 102, in the direction of arrow 122.

As an alternative to manually pinching the pivoting hooks, a triggering mechanism 124 is linked to the releasable retaining mechanism 116. When the triggering mechanism 124 is activated, the triggering mechanism 124 causes the releasable retaining mechanism 116 to pivot outward and release the engaging mechanism 118 from the releasable retaining mechanism 116. When the engaging mechanism 118 is released from the retaining mechanism 116, the bias, or action of the compressed spring biasing element 114 pushes the sliding weight 110 towards the first end 104 of the guide rod 102, where it impacts the striking member 108. Other methods and mechanisms for holding the sliding weight 110 in place and for releasing the sliding weight 110 may be utilized.

Figure 2B:
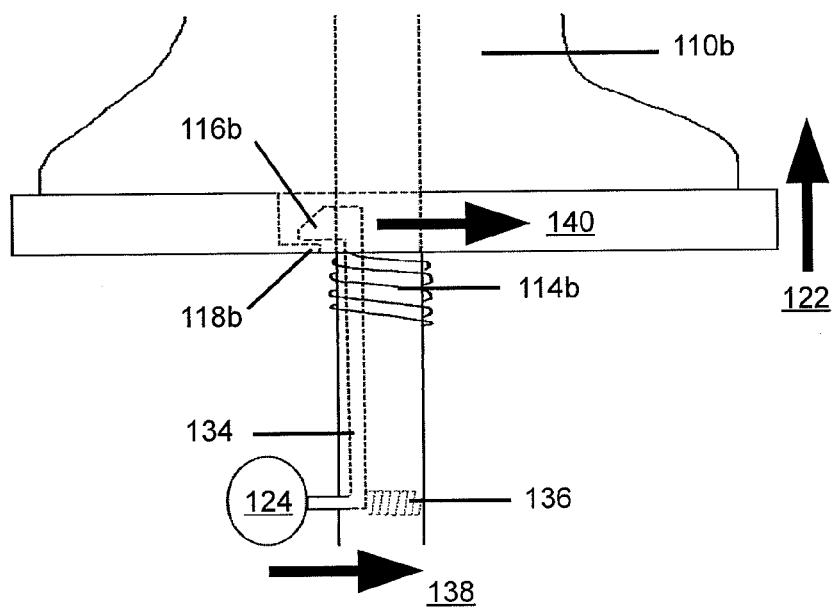
FIG. 2b is a fragmentary cross sectional illustration of a slap hammer according to another embodiment of the invention.

FIG. 2b is a fragmentary cross sectional illustration of a slap hammer according to another embodiment of the invention. A sliding weight 110b is held in place against the action of a biasing element 114b by a releasable retaining mechanism 116b which engages an engaging mechanism 118b of the sliding weight 110b. The releasable retaining mechanism 116b is mechanically connected to the triggering mechanism 124 via a connecting member 134. The triggering mechanism 124 and the releasable retaining mechanism 116b are normally held in a locked position by a trigger biasing element 136, shown as a compression spring. As shown in FIG. 2b, the connecting mechanism 134, the trigger biasing element 136, and the releasable retaining mechanism 116b are, in whole or in part, contained inside the guide rod.

The slap hammer is operated by initially sliding the sliding weight 110b 'downward' along the guide rod toward the first end 104 of the guide rod 102. As shown in FIG. 2b, the sliding weight slides downward and over the releasable retaining mechanism 116b, temporarily moving the releasable retaining mechanism 116b inward, into the guide rod. As the sliding weight 110b continues to move down, the releasable retaining mechanism 116b will clear the engaging mechanism 118b, and the releasable retaining mechanism 116b will "pop" out and revert back into a locked position, where it engages the engaging mechanism 118b to hold the sliding weight 110b against the bias of the biasing element 114b. The releasable retaining mechanism 116b normally reverts into the locked position due to the constant bias of the trigger biasing element 136, which holds the trigger 124 and the releasable retaining mechanism 116b in place.

When an operator wants to activate the slap hammer, the triggering mechanism 124 can be pushed or triggered. As shown in FIG. 2b, the triggering mechanism 124 is pushed inward, in the direction of arrow 138, and against the action of the trigger biasing element 136. As the triggering mechanism 124 moves in the direction of the arrow 138, the releasable retaining mechanism 116b moves in tandem with the movement of the triggering mechanism 124, in the direction of arrow 140. Eventually the engaging mechanism 118b will clear the retracting releasable retaining mechanism 116b as is moves inward, thereupon releasing the sliding weight 110b, and letting the biasing element 114b push the sliding weight 110b upward in the direction of arrow 122, toward the second end 106 of the guide rod 102 and with the action of the biasing element 114b.

Figure 3:
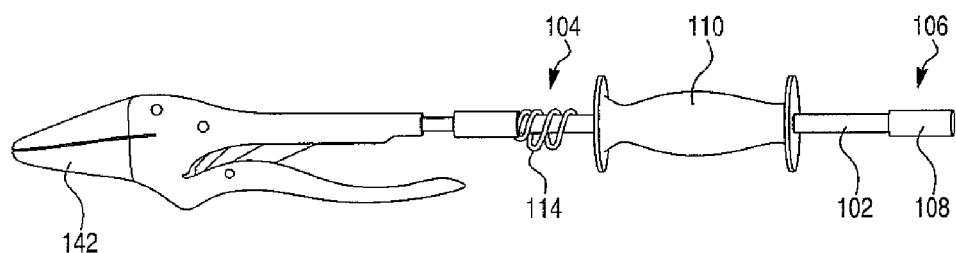
FIG. 3 is a schematic view of a slap hammer according to another embodiment of the invention.

FIG. 3 is a perspective view of a slap hammer according to another embodiment of the invention. In FIG. 3, a slap hammer comprises a guide rod 102 having a first end 104 and a second end 106. The slap hammer also includes a sliding weight 110 that slides along the guide rod 102. The guide rod 102 of the slap hammer shown in FIG. 3 further comprises a coupling mechanism in the form of pliers 142. The pliers 142 can clamp on an object to be removed from a surgical area. Once the pliers 142 are clamped to an object, the sliding weight 110 can be released from a locked position at the first end 104 of the guide rod, and propelled by the tension of the spring biasing element 114 towards the second end 106 of the guide rod 102, where it will impact the striking member 108, and impart a pulling force on the object clamped by the pliers 142. In some devices, the pliers 142 may be substituted with other connecting mechanisms, such as the ones shown in FIG. 4. In other devices, the pliers 142 are permanently attached to the slap hammer.

Figure 4:
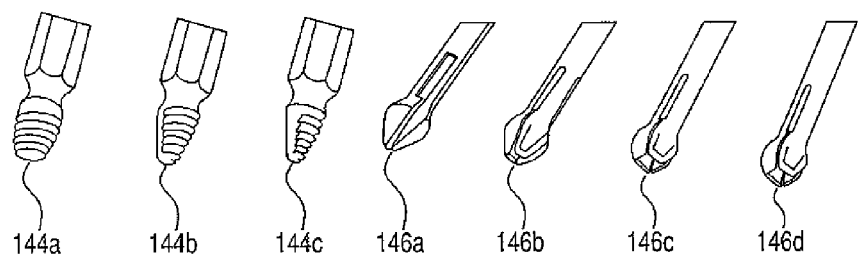
FIG. 4 is a series of schematic views of connecting mechanisms according to embodiments of the invention.

FIG. 4 is an illustration of various connecting mechanisms according to embodiments of the invention. The first end 104 of the guide rod 102 can be configured to accept a variety of different connecting mechanisms, such as screw 120 or pliers 142. Other off-the-shelf and/or custom made products can be used. As shown in FIG. 4, other connecting mechanisms comprise various threaded screw endings 144a, 144b, and 144c. Alternatively, various connecting mechanisms comprise pin connectors 146a, 146b, 146c, 146d which are advantageous for clamping around smaller objects, such as wire.

Figure 5:
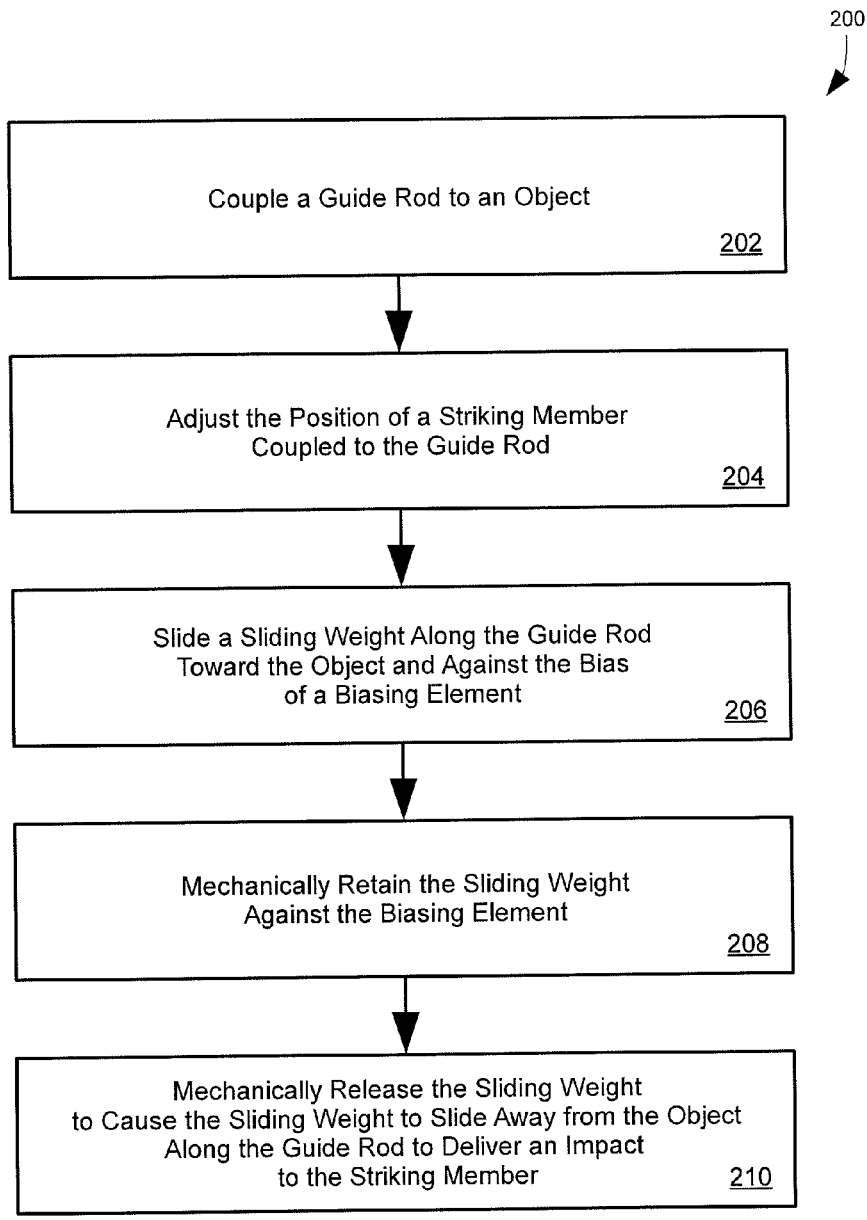
FIG. 5 is a flow chart of a method for using a slap hammer according to another embodiment of the invention.

FIG. 5 is an illustration of a method 200 for using a slap hammer according to another embodiment of the invention. The method 200 begins by coupling a guide rod to an object 202. The guide rod may be coupled to the object, i.e. the target workpiece, via a coupling mechanism, such as a threaded screw, pliers, a clamp, a ring, or a hook. In other embodiments, other coupling mechanisms may be used, such as a magnet, or a vacuum suction coupling mechanism. The object coupled to the guide rod may be surgical instrument, or some other object.

The force applied to the object may be controlled by optionally adjusting the position of a striking member on the guide rod 204. The striking member is positioned on a second end of the guide rod opposite the first end of the guide rod and the object coupled to the guide rod (i.e. the target workpiece). By moving the striking member relative to the first end of the guide rod, the acceleration of the sliding weight may be increased or decreased, and thus the force delivered by the sliding weight may be adjusted. The striking member can be adapted to move along the guide toward or away from the first end of the guide rod in order to adjust the position of the striking member relative to the sliding weight. In some embodiments, step 204 follows step 208—that is, the position of the striking member is adjusted after the sliding weight is mechanically retained against the biasing element 208.

After the guide rod is coupled to the object 202 and the position of the striking member is adjusted 204, a sliding weight is moved, or slid, along the guide rod toward the object and against the bias of a biasing element 206. As the sliding weight is slid towards the object 206, the biasing element may store potential energy. For example, a biasing element in the form of a compression spring will compress and store potential energy.

While or immediately after the sliding weight is positioned against the bias of the biasing element, the sliding weight is mechanically retained against the biasing element 208. A temporary locking mechanism, i.e. a releasable retaining mechanism, releasably retains the sliding weight against the bias or pressure of the biasing element.

Finally, the sliding weight is mechanically released from the temporary locking mechanism, causing the sliding weight to slide away from the object along the guide to deliver an impact to the striking member 210. A triggering mechanism may mechanically release the sliding weight from the temporary locking mechanism. When the sliding weight impacts the striking member, the slap hammer moves or jerks in the same direction traveled by the sliding weight, potentially moving or dislodging the object coupled to the slap hammer in the same direction.

This invention is susceptible to considerable variation in its practice. Therefore the foregoing description is not intended to limit, and should not be construed as limiting the invention to the particular exemplifications presented hereinabove. Rather, what is intended to be covered is as set forth in the ensuing claims and the equivalents thereof permitted as a matter of law.

What is claimed is:

1. A slap hammer comprising:
   a guide rod having a first end and a second end, said guide rod defining a longitudinal axis;
   a striking member disposed on the guide rod adjacent to the second end of the guide rod, said striking member being selectively positioned at different positions along said longitudinal axis of the guide rod, wherein the striking member is coupled to the guide rod by a latching mechanism;
   a sliding weight slidable along the guide rod between the first end of the guide rod and the striking member;
   a biasing element positioned between the sliding weight and the first end of the guide rod, the biasing element biasing the sliding weight towards the second end of the guide rod; and
   a releasable retaining mechanism for releasably retaining the sliding weight against the action of the biasing element.

2. The slap hammer according to claim 1 further comprising a coupling mechanism at the first end of the guide rod.

3. The slap hammer according to claim 2 wherein the coupling mechanism comprises a threaded screw, pliers, a clamp, a ring, or a hook.

4. The slap hammer according to claim 2, wherein the coupling mechanism is interchangeable.

5. The slap hammer according to claim 1 wherein the sliding weight comprises an opening through which the guide rod extends.

6. The slap hammer according to claim 1 wherein the biasing element comprises a compression spring or a tensioning spring.

7. The slap hammer according to claim 1 wherein the releasable retaining member comprises a pivoting hook.

8. The slap hammer according to claim 7 wherein the sliding weight comprises a collar, wherein the pivoting hook releasably engages the collar.

9. The slap hammer according to claim 1 further comprising a trigger mechanism for triggering the release of the sliding weight.

* * * * *